(12) United States Patent
Chan et al.

(10) Patent No.: US 11,786,662 B2
(45) Date of Patent: *Oct. 17, 2023

(54) AMPULE AUTOINJECTOR SYSTEMS AND METHODS

(71) Applicant: University of Washington, Seattle, WA (US)

(72) Inventors: Keith Chan, Seattle, WA (US); Ben Carney, Seattle, WA (US); Zachary Chen, Seattle, WA (US); Ha Seung Chung, Seattle, WA (US); Jazmine Saito, Seattle, WA (US); Wealth Mele Salvador, Seattle, WA (US); Shawn Swanson, Seattle, WA (US)

(73) Assignee: UNIVERSITY OF WASHINGTON, Seattle, WA (US)

( * ) Notice: Subject to any disclaimer, the term of this patent is extended or adjusted under 35 U.S.C. 154(b) by 839 days.

This patent is subject to a terminal disclaimer.

(21) Appl. No.: 16/703,808

(22) Filed: Dec. 4, 2019

(65) Prior Publication Data
US 2020/0108205 A1 Apr. 9, 2020

Related U.S. Application Data

(63) Continuation of application No. 15/480,029, filed on Apr. 5, 2017, now Pat. No. 10,532,157.
(Continued)

(51) Int. Cl.
*A61M 5/24* (2006.01)
*A61M 5/20* (2006.01)
(Continued)

(52) U.S. Cl.
CPC ............ *A61M 5/2466* (2013.01); *A61M 5/19* (2013.01); *A61M 5/2033* (2013.01);
(Continued)

(58) Field of Classification Search
CPC ...... A61M 5/19; A61M 5/2466; A61M 5/288; A61M 2005/247; A61M 2005/2407; A61M 5/284
See application file for complete search history.

(56) References Cited

U.S. PATENT DOCUMENTS 2,390,246 A  10/1940  Folkman
2,545,017 A   6/1947  Billingsley
(Continued)

OTHER PUBLICATIONS

2016 Health Innovation Challenge (HIC) conference, "EpiForAll" PowerPoint presentation.
(Continued)

*Primary Examiner* — Tiffany Legette
(74) *Attorney, Agent, or Firm* — McDonnell Boehnen Hubert & Berghoff LLP

(57) ABSTRACT

An autoinjector is described that includes an outer body, a first trigger, an output needle, and a first compartment. The first compartment is positioned within the outer body and includes (i) a main body, (ii) a first biasing member coupled to the first trigger, and (iii) a protrusion positioned at a distal end of the main body. The autoinjector further includes a second compartment positioned in the outer body and in fluid communication with the first compartment and the output needle. The autoinjector also includes a second biasing member coupled to a second trigger. The first biasing member is configured to, upon application of force to the first trigger, automatically move an ampule in a distal direction relative to the main body to force the ampule against the protrusion, so as to break the ampule and allow a medicament to flow from the ampule to the second compartment.

19 Claims, 9 Drawing Sheets

Related U.S. Application Data

(60) Provisional application No. 62/320,286, filed on Apr. 8, 2016.

(51) Int. Cl.
*A61M 5/315* (2006.01)
*A61M 5/19* (2006.01)
*A61M 5/28* (2006.01)
*A61M 5/31* (2006.01)
*A61M 5/32* (2006.01)

(52) U.S. Cl.
CPC .......... *A61M 5/288* (2013.01); *A61M 5/3145* (2013.01); *A61M 5/31591* (2013.01); *A61M 5/3243* (2013.01); *A61M 2005/208* (2013.01); *A61M 2005/2013* (2013.01); *A61M 2005/2026* (2013.01); *A61M 2005/247* (2013.01); *A61M 2005/2407* (2013.01); *A61M 2005/3128* (2013.01); *A61M 2205/581* (2013.01)

(56) References Cited

U.S. PATENT DOCUMENTS

| | | |
|---|---|---|
| 2,609,818 A | 9/1952 | Parrine |
| 2,753,866 A | 7/1956 | Koree |
| 3,892,237 A | 7/1975 | Steiner |
| 3,974,831 A | 8/1976 | Malmin |
| 4,689,042 A | 8/1987 | Sarnoff et al. |
| 5,393,497 A | 2/1995 | Haber et al. |
| 5,628,353 A | 5/1997 | Ruther |
| 6,099,510 A | 8/2000 | Ruther et al. |
| 6,743,203 B1 | 6/2004 | Pickhard |
| 6,902,543 B1 * | 6/2005 | Cherif-Cheikh ............ A61M 5/31596 604/82 |
| 7,449,012 B2 | 11/2008 | Young et al. |
| 2002/0049407 A1 | 4/2002 | Hill et al. |
| 2012/0041379 A1 | 2/2012 | Macarthur et al. |
| 2012/0101475 A1 | 4/2012 | Wilmot et al. |
| 2013/0032623 A1 | 2/2013 | Kayser |
| 2014/0276385 A1 | 9/2014 | Buchine et al. |
| 2015/0065992 A1 | 3/2015 | Korkuch et al. |
| 2015/0329339 A1 | 11/2015 | Oberli et al. |
| 2017/0232196 A1 | 8/2017 | Constantineau et al. |
| 2018/0028753 A1 | 2/2018 | Wilmot et al. |

OTHER PUBLICATIONS

2016 Health Innovation Challenge (HIC) conference, "EpiForAll" poster presentation.
"Epi for All," Business Handout 2016.

* cited by examiner

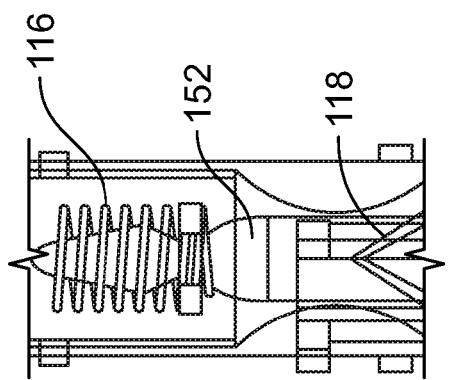
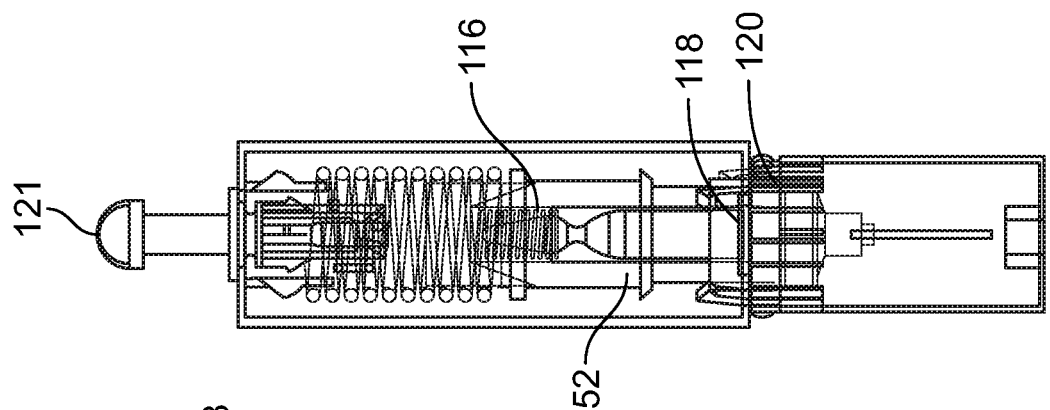
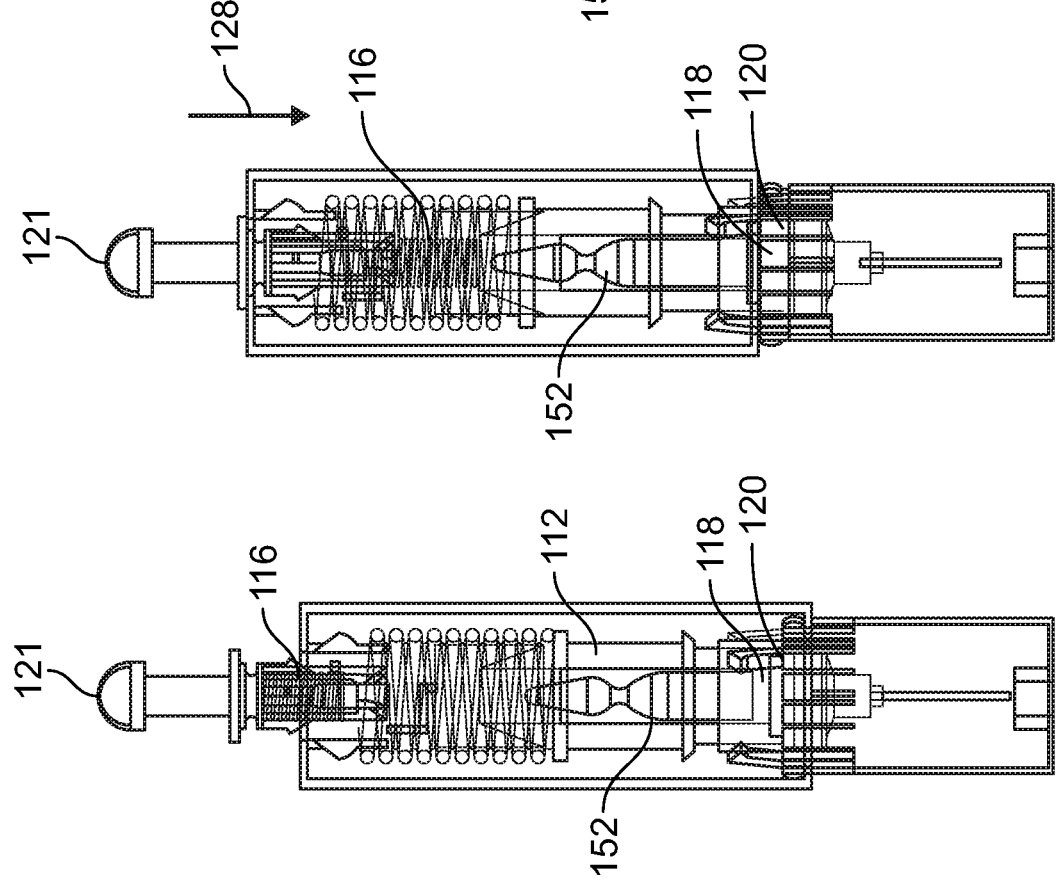
FIG. 9A  FIG. 9B  FIG. 9C  FIG. 9D

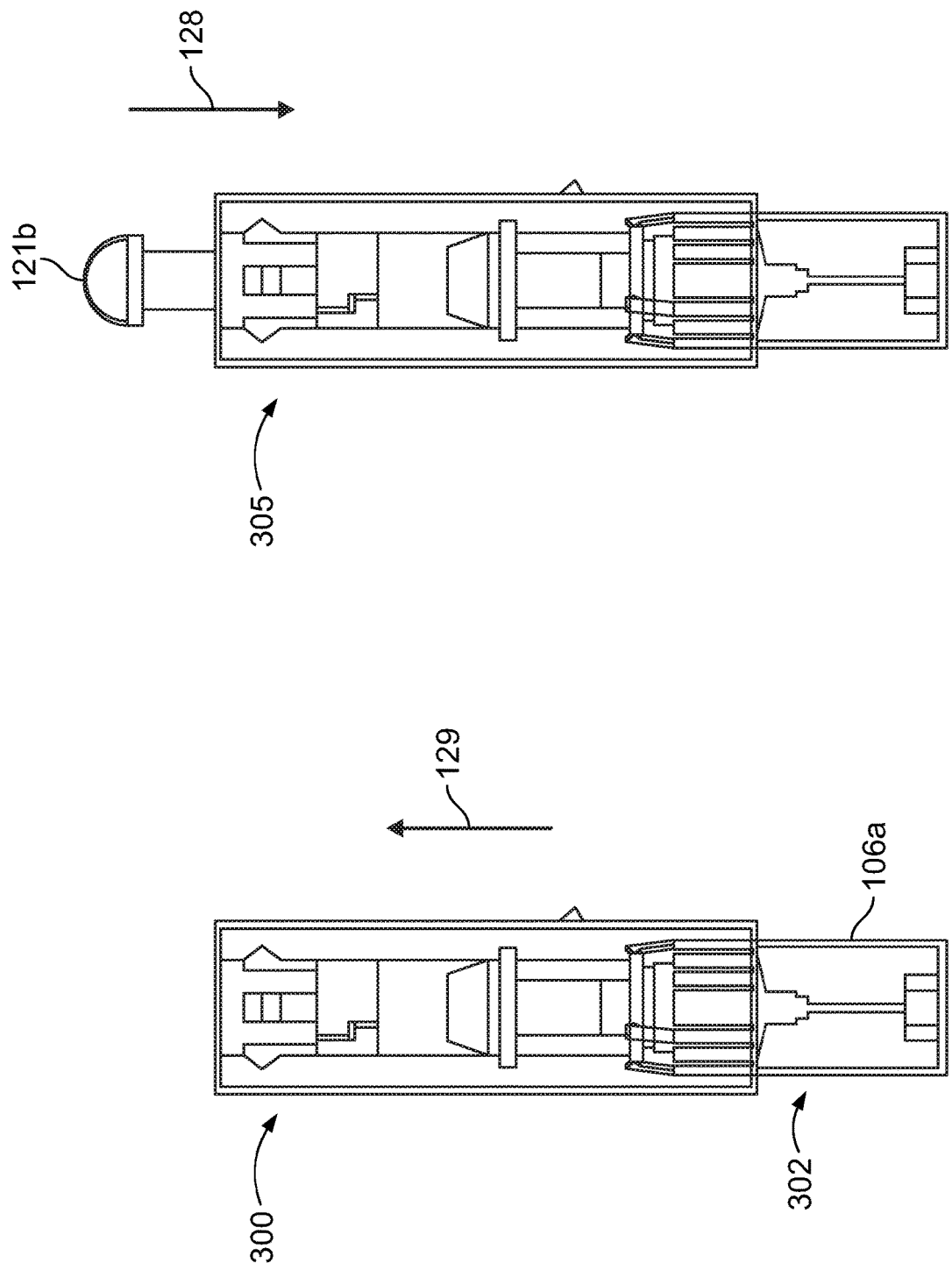

AMPULE AUTOINJECTOR SYSTEMS AND METHODS

CROSS-REFERENCE TO RELATED APPLICATIONS

This application claims priority to U.S. Non-Provisional application Ser. No. 15/480,029, filed on Apr. 5, 2017 that in turn claims priority to U.S. Provisional Patent Application Ser. No. 62/320,286, filed on Apr. 8, 2016, and entitled "Glass ampule autoinjector," the full disclosures of which are incorporated herein by reference.

FIELD

The present disclosure generally relates to drug delivery devices, and more particularly to, autoinjectors configured to inject medicament from an ampule by automatically breaking the ampule and subsequently automatically injecting the medicament.

BACKGROUND

Automatically injecting a drug (such as epinephrine, insulin, glucagon, atropine, amiodarone, dextrose, naloxone) using an autoinjector offers numerous advantages over manually injecting the drug using a manual injector. For instance, current methods of manually injecting drugs typically involve a user manually breaking an ampule holding the drug, transferring the drug from the ampule to a syringe, and then injecting the drug using the syringe. However, one example drawback of manual injection is that numerous separate components must be available to a user immediately upon need for the drug. For example, a syringe with a suitably long needle and an ampule of unexpired epinephrine must be available immediately in the event of anaphylaxis. However, in practice, it is often difficult and/or inconvenient for users to carry these items around at all times. On the other hand, an autoinjector provides a single device pre-filled with a drug and, in practice, it is easier and more convenient for a user to have a single device pre-filled with a drug compared to having the multiple components needed for manual injection.

Another example drawback of manual injection is that intramuscular injection is often difficult for an individual without medical training to execute successfully. For instance, the user must know the correct dose to administer based on the patient's weight and then translate that into the correct volume of drug solution to apply (e.g., since the drug concentrations may vary). As a result, manual injections are typically performed by a trained medical professional due to the difficulty of the manual injection. On the other hand, autoinjectors for automatically injecting a drug eliminate the need for product assembly and dosage calculation, thus making self-injection both easier and safer.

However, current autoinjectors for injecting drugs such as epinephrine have numerous drawbacks. For instance, current autoinjectors for automatically injecting epinephrine typically include drug bottles having a membrane top or pre-filled syringes. However, manufacturing autoinjectors with such drug bottles or pre-filled syringes involves aseptic manufacturing, and this increases the cost of production of the autoinjector. Further, autoinjectors with these drug bottles or pre-filled syringes are typically classified as drug/device combination and are thus subject to an expensive and time consuming regulatory approval process. This approval process in turn makes current autoinjectors typically substantially more expensive than current methods of manual injection. Furthermore, current autoinjectors are typically manufactured with a drug bottle or pre-filled syringe that is non-removable. However, since epinephrine expires after approximately 18 months, the entire autoinjector must be replaced when the epinephrine within the autoinjector expires.

SUMMARY

In one example, an autoinjector is described that includes an outer body, a first trigger, an output needle, and a first compartment. The first compartment is positioned within the outer body and includes (i) a main body, (ii) a first biasing member coupled to the first trigger, and (iii) a protrusion positioned at a distal end of the main body. The autoinjector further includes a second compartment positioned in the outer body and in fluid communication with the first compartment and the output needle. The autoinjector also includes a second biasing member coupled to a second trigger. The first biasing member is configured to, upon application of force to the first trigger, automatically move an ampule when loaded in the main body in a distal direction relative to the main body to force the ampule against the protrusion, so as to break the ampule and allow a medicament within the ampule to flow from the ampule to the second compartment. The second biasing member is configured to, upon application of force to the second trigger, automatically move the first compartment in the distal direction relative to the outer housing and the second compartment to force medicament from the second compartment to the output needle.

In another example, an autoinjector is described that includes an outer body, a first trigger, an output needle, and a first compartment. The first compartment is positioned within the outer body and comprises (i) a main body and (ii) a first biasing member coupled to the first trigger. The autoinjector also includes a second compartment positioned in the outer body and in fluid communication with the first compartment and the output needle. Further, the autoinjector includes a second biasing member coupled to a second trigger. The first biasing member is configured to, upon application of force to the first trigger, automatically move an ampule when loaded in the main body relative to the main body to force the ampule against a portion of the first compartment, so as to break the ampule and allow a medicament within the ampule to flow from the ampule to the second compartment. The second biasing member is configured to, upon application of force to the second trigger, automatically force medicament from the second compartment to the output needle.

In yet another example, an autoinjector is described that includes an outer body, a trigger, an output needle, and a first compartment. The first compartment is positioned within the outer body and comprises (i) a main body and (ii) a first biasing member coupled to the trigger. The autoinjector also includes a second compartment positioned in the outer body and in fluid communication with the first compartment and the output needle. Further, the autoinjector includes a second biasing member coupled to the trigger. The first biasing member is configured to, upon application of force to the trigger, automatically move an ampule when loaded in the main body relative to the main body to force the ampule against a portion of the first compartment, so as to break the ampule and allow a medicament within the ampule to flow from the ampule to the second compartment. The second biasing member is configured to, upon the application of force to the trigger, automatically force medicament from the second compartment to the output needle.

In still yet another example, a method of automatically injecting a medicament is described. The method includes an autoinjector receiving into a first compartment an ampule holding a medicament. The method further includes in response to application of force to a first trigger, a first biasing member automatically moving the ampule relative to a main body of the first compartment, so as to break the ampule and allow the medicament within the ampule to flow from the ampule to a second compartment of the autoinjector. Still further, the method includes in response to application of force to a second trigger, a second biasing member automatically forcing medicament from the second compartment to an output needle of the autoinjector.

The features, functions, and advantages that have been discussed can be achieved independently in various embodiments or may be combined in yet other embodiments further details of which can be seen with reference to the following description and drawings.

BRIEF DESCRIPTION OF THE FIGURES

The novel features believed characteristic of the illustrative embodiments are set forth in the appended claims. The illustrative embodiments, however, as well as a preferred mode of use, further objectives and descriptions thereof, will best be understood by reference to the following detailed description of an illustrative embodiment of the present disclosure when read in conjunction with the accompanying drawings.

FIGS. 9a-d illustrate side views of various components of the example autoinjector of FIG. 1 during breaking of an ampule, according to an example embodiment.

FIG. 11 illustrates a side view of an example autoinjector, according to an example embodiment.

FIG. 12 illustrates a side view of an example autoinjector, according to an example embodiment.

DETAILED DESCRIPTION

Disclosed embodiments will now be described more fully hereinafter with reference to the accompanying drawings, in which some, but not all of the disclosed embodiments are shown. Indeed, several different embodiments may be described and should not be construed as limited to the embodiments set forth herein. Rather, these embodiments are described so that this disclosure will be thorough and complete and will fully convey the scope of the disclosure to those skilled in the art.

As mentioned above, current systems and methods for automatically injecting epinephrine have a number of drawbacks. The methods and systems in accordance with the present disclosure beneficially provide improved methods and systems for automatically injecting a medicament such as epinephrine. In particular, the methods and systems in accordance with the present disclosure beneficially provide for automatically injecting medicament from an ampule holding a medicament by automatically breaking the ampule holding the medicament and subsequently automatically injecting that medicament.

In one example, an autoinjector is described that includes an outer body, a first trigger, an output needle, and a first compartment. The first compartment is positioned within the outer body and includes (i) a main body, (ii) a first biasing member coupled to the first trigger, and (iii) a protrusion positioned at a distal end of the main body. The autoinjector further includes a second compartment positioned in the outer body and in fluid communication with the first compartment and the output needle. The autoinjector also includes a second biasing member coupled to a second trigger. The first biasing member is configured to, upon application of force to the first trigger, automatically move an ampule when loaded in the main body in a distal direction relative to the main body to force the ampule against the protrusion, so as to break the ampule and allow a medicament within the ampule to flow from the ampule to the second compartment. The second biasing member is configured to, upon application of force to the second trigger, automatically move the first compartment in the distal direction relative to the outer housing and the second compartment to force medicament from the second compartment to the output needle.

Figure 2:
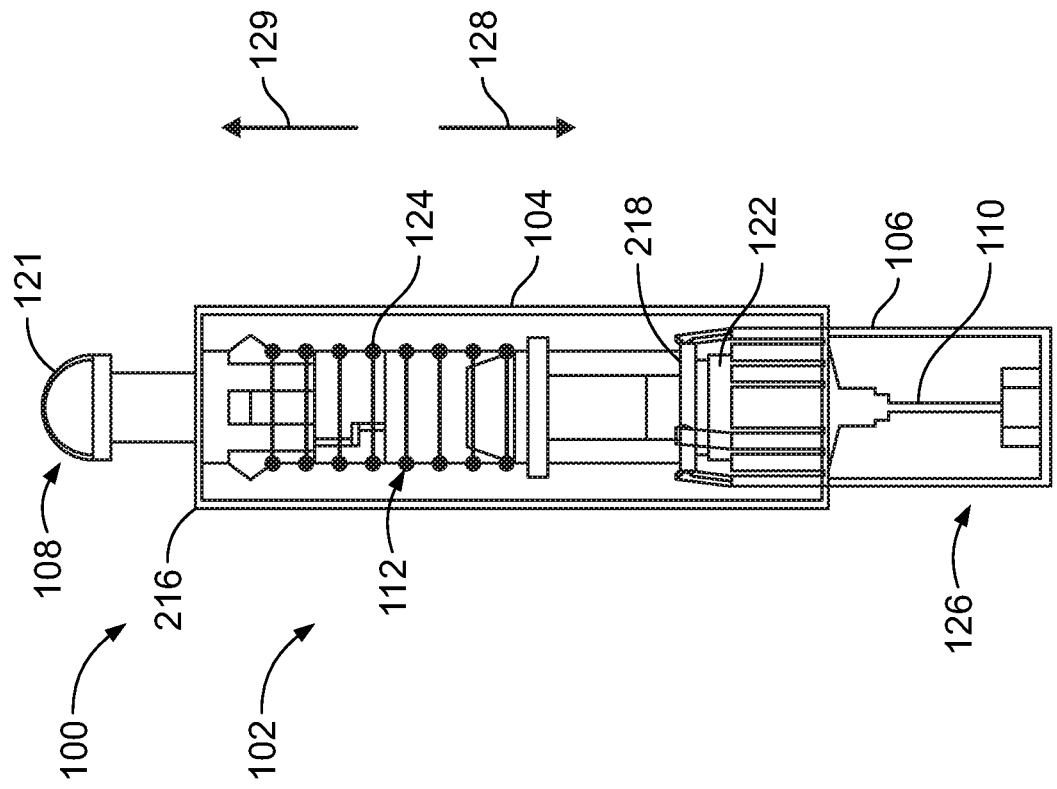
FIG. 2 illustrates a side view of the example autoinjector of FIG. 1 showing various internal components, according to an example embodiment.
Figure 1:
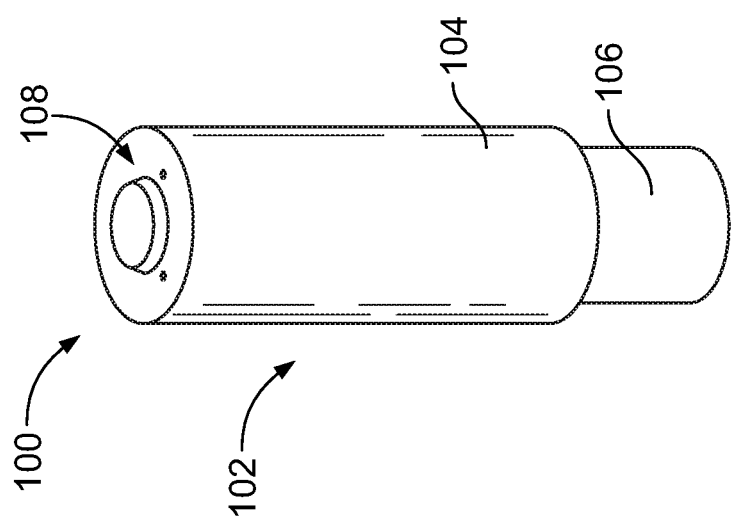
FIG. 1 illustrates an example autoinjector, according to an example embodiment.
Figure 3:
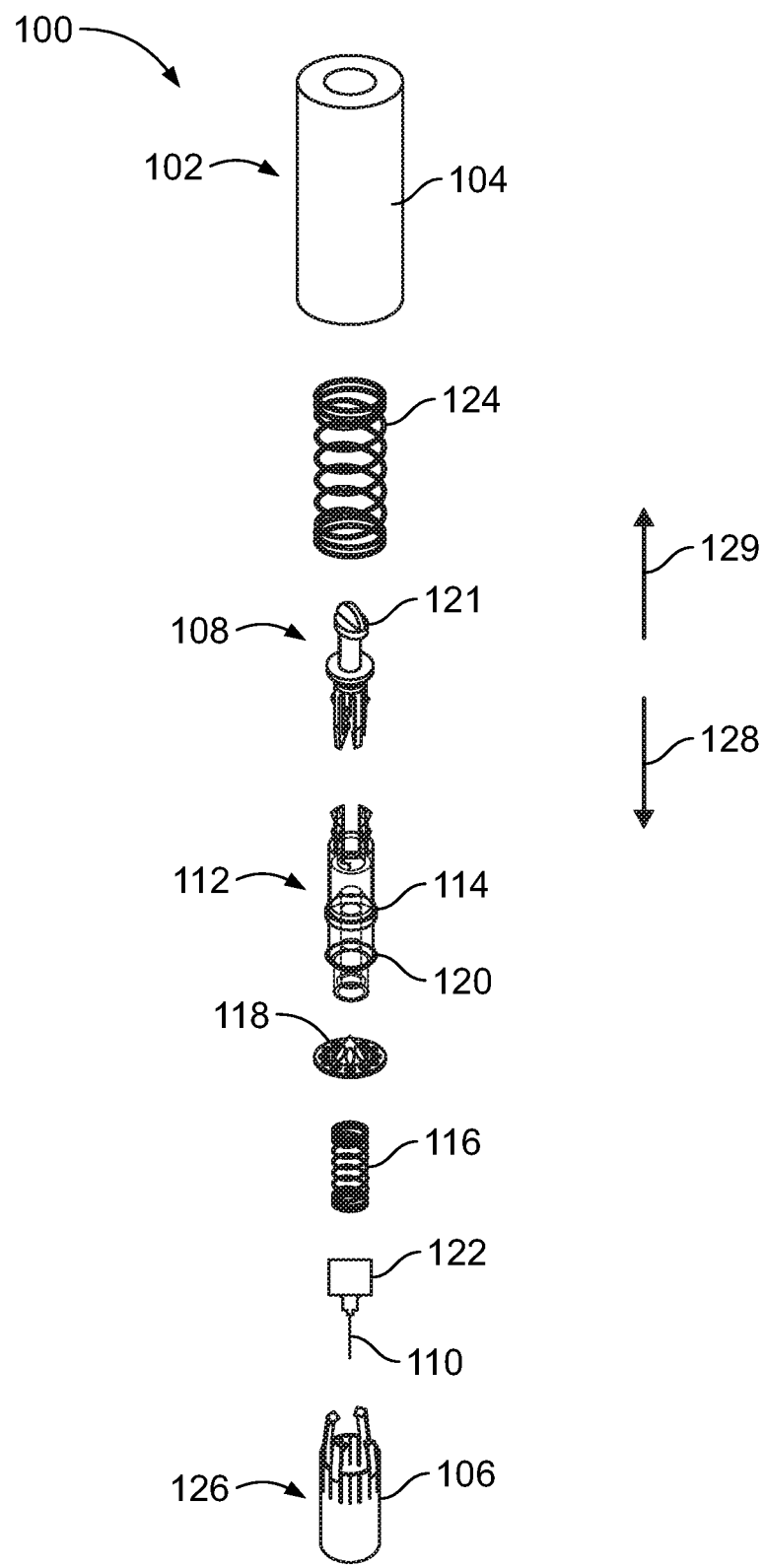
FIG. 3 illustrates an exploded view of the example autoinjector of FIG. 1, according to an example embodiment.

Referring now to FIGS. 1-3, an example autoinjector 100 is illustrated. The autoinjector 100 includes an outer body 102. Outer body 102 includes a main outer body 104 and a needle shield 106 slidably engaged with the main outer body 104. Autoinjector 100 further includes a first trigger 108, an output needle 110, and a first compartment 112. The first compartment 112 is positioned within the outer body 102 and includes (i) a main body 114, (ii) a first biasing member 116 coupled to the first trigger 108, and (iii) a protrusion 118 positioned at a distal end 120 of the main body 114. The autoinjector 100 also includes a cap 121. Cap 121 is configured to be inserted into the first compartment 112 and cap 121 acts as the first trigger 108.

The autoinjector 100 further includes a second compartment 122 positioned in the outer body 102 and in fluid communication with the first compartment 112 and the output needle 110. The autoinjector 100 also includes a second biasing member 124 coupled to a second trigger 126. The needle shield 106 acts as the second trigger 126.

The first biasing member 116 is configured to, upon application of force to the first trigger 108, automatically move an ampule when loaded in the main body 114 in a distal direction 128 relative to the main body 114 to force the ampule against the protrusion 118, so as to break the ampule and allow a medicament within the ampule to flow from the ampule to the second compartment 122. Further, the second biasing member 124 is configured to, upon application of force to the second trigger 126, automatically move the first compartment 112 in the distal direction 128 relative to the outer housing 102 and the second compartment 122 to force medicament from the second compartment 122 to the output needle 110.

Prior to injection, an ampule holding a medicament may be loaded into autoinjector 100. For instance, with reference to FIG. 4, the first compartment 112 includes an opening 150 configured to allow for loading of an ampule in the main body 114 and removal of an ampule when loaded in the main body 114. Opening 150 is also configured to receive cap 121 (see FIGS. 2 and 5). In order to load the ampule, a user may remove cap 121 from opening 150 by moving cap 121 in proximal direction 129. The user may then insert an ampule into first compartment 112. After loading the ampule in the autoinjector, a user may then insert the cap 121 back into the first compartment 112. FIG. 9A illustrates an example ampule 152 when loaded in the first compartment 112. By allowing a user to insert and remove ampule 152, the autoinjector 100 beneficially allows a user to remove the ampule 152 if the medicament within the ampule 152 has expired and to reinsert a new ampule in the autoinjector 100.

In an example embodiment, the ampule 152 is a glass ampule holding epinephrine. However, the ampule 152 may be formed from other materials and may hold other medicaments. For instance, in other examples, the medicament held within the ampule 152 is insulin, glucagon, atropine, amiodarone, dextrose, or naloxone. Other medicaments are possible as well. Further, rather than being formed from glass, in other examples the ampule 152 is formed from plastic or any other suitable material. Generally, ampule 152 may be formed from any material that may be shattered, punctured, or otherwise broken, so as to allow medicament to flow out of the broken ampule 152.

Further, although in this example the ampule 152 is loaded into opening 150 in a proximal end of the first compartment 112, the ampule 152 may be loaded into the autoinjector 100 in other ways. For instance, in another example embodiment, the outer body 102 and the main body 114 of the first compartment 112 each include a longitudinally-extending door along the outer body 102 and the main body 114. These longitudinally-extending doors may be opened and closed to allow for insertion and removal of the ampule 152 via the longitudinally-extending doors.

After ampule 152 is loaded into the autoinjector 100, a user may activate the autoinjector 100 to automatically break the ampule 152 holding the medicament and then subsequently automatically inject the medicament within the ampule 152. Release of the first biasing member 116 serves to break the ampule 152 and release of the second biasing member 124 serves to automatically inject the medicament within the ampule 152.

Figure 4:
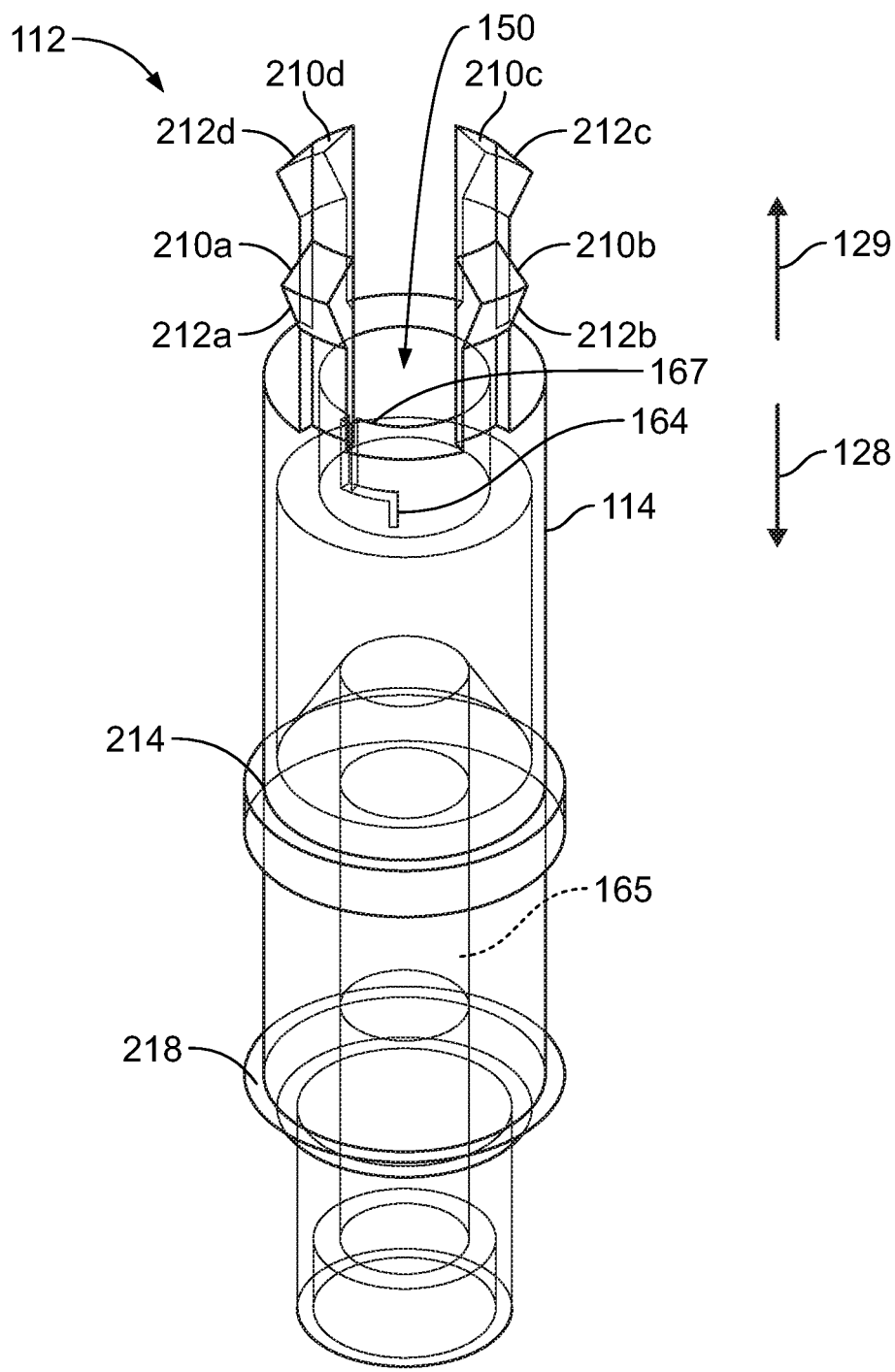
FIG. 4 illustrates a perspective view of an example first compartment of the example autoinjector of FIG. 1, according to an example embodiment.
Figure 5:
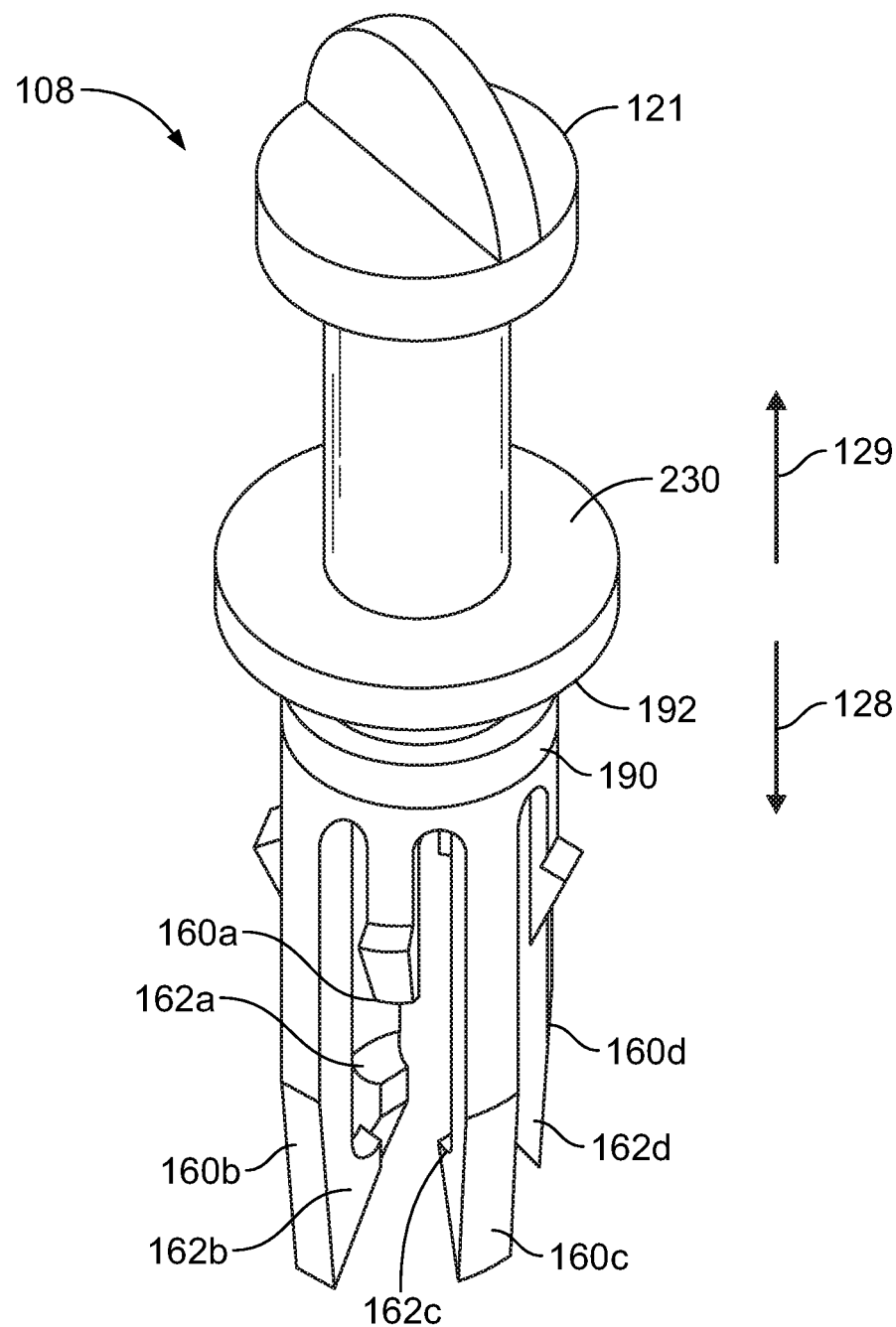
FIG. 5 illustrates a perspective view of an example cap of the example autoinjector of FIG. 1, according to an example embodiment.

The first biasing member 116 automatically breaking the ampule 152 is described in further detail with respect to FIGS. 4-5 and 9A-9D. As mentioned above, the first biasing member 116 is configured to, upon application of force to the first trigger 108, automatically move an ampule when loaded in the main body 114 in a distal direction 128 relative to the main body 114 to force the ampule against the protrusion 118, so as to break the ampule and allow a medicament within the ampule to flow from the ampule to the second compartment 122. In an example embodiment, the cap 121 includes at least one arm having a protrusion configured to hold the first biasing member 116 in a compressed state. The at least one arm is configured to, upon application of force to the cap 121, deflect to release the first biasing member 116 from the at least one arm having the protrusion. For instance, as shown in FIG. 5, cap 121 includes arms 160a-d and the arms 160a-d include protrusions 162a-d. These protrusions 162a-d act to hold the biasing member 116 in a compressed state (see FIG. 9A).

A user may apply force to the trigger 108 in order to activate the trigger 108. In an example embodiment, a user may press trigger 108 in distal direction 128. Upon application of the force to the first trigger 108, the cap 121 moves in the distal direction 128. This movement causes the arms 160a-d to interact with inner surface 164 (see FIG. 4) of the first compartment 112. The arms 160a-d deflect radially outward as a result of this interaction. This deflection of the arms 160a-d allows the biasing member 116 to be released from the protrusions 162a-d of the arms 160a-d (see FIG. 9B). When biasing member 116 is released, biasing member 116 then biases ampule 152 in the distal direction 128 relative to main body 114 to force ampule 152 against the protrusion 118 positioned at the distal end 120 of the main body 114 (see FIGS. 9B-9D). Movement of the ampule 152 relative to the main body 114 and the protrusion 118 causes the protrusion 118 to pierce the ampule 152. FIG. 9D is a close-up view of the protrusion 118 piercing the ampule 152. Although in this example, the arms 160a-d deflect radially outward to release the biasing member 116 from protrusions 162a-d, in another example, the arms 160a-d and protrusions 162a-d are configured to deflect radially inward to release the biasing member 116.

Biasing member 116 forces ampule 152 against protrusion 118 with a sufficient force to cause ampule 152 to break. In an example, biasing member 116 is a spring. Any suitable spring may be used. In an example embodiment, the spring constant is approximately 4-10 pounds per inch (lbs/in) and the spring provides approximately 4-10 pounds of force (lbf). Other example spring constants and pounds of force are possible as well.

In an example embodiment, protrusion 118 is a spike. For instance, as shown in FIG. 6, spike assembly 168 includes protrusion 118. Protrusion 118 includes a sharp point 170 that acts as the spike. Providing a protrusion having sharp point 170 helps to reduce or minimize the amount of force required from the biasing member 116 to break the ampule 152 when the ampule is forced against the protrusion 118.

Figure 6A:
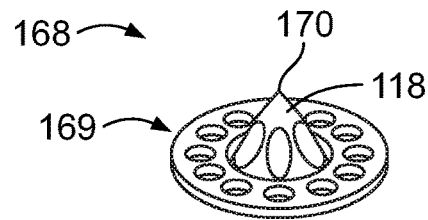
FIGS. 6a-b illustrate, respectively, a perspective view and a side view of an example spike assembly of the example autoinjector of FIG. 1, according to an example embodiment.
Figure 6B:
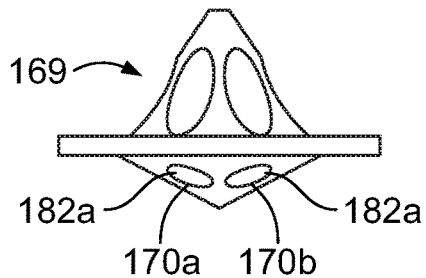

Although in the example shown in FIGS. 3 and 6a-b, the first compartment 112 includes a single protrusion 118 positioned at the distal end 120 of the first compartment 112, other examples are possible as well. As a general matter, ampule 152 may be forced against any portion of the first compartment 112 with a sufficient force to break the ampule 152. In an example embodiment, first compartment 112 includes a plurality of protrusions at the distal end 120 and each protrusion forms a spike. In another example embodiment, the distal end 120 of the first compartment 112 is a flat or substantially flat distal end. In such an example, the biasing member 116 may force the ampule 152 against the flat or substantially flat distal end with a sufficient force to break the ampule 152. In yet another example embodiment, rather than including a protrusion 118 at the distal end 120 of the main body 114, the main body 114 includes one or more protrusions that extend radially inward from a sidewall 165 (see FIG. 4) of the main body 114. When biasing member forces the ampule 152 in the distal direction 128, the ampule 152 may be forced against these protrusions extending radially inward and this may cause the ampule 152 to break. Other examples are possible as well.

Further, although in the illustrated example, the ampule 152 is moved in distal direction 128 relative to the main body 114 of the first compartment 112, in other example embodiments the ampule may be broken in other ways. For instance, the ampule may be forced in other directions, such as proximal direction or sideways. As a general matter, in example embodiments, energy is applied to the ampule 152 in order to cause the ampule to break. Any suitable energy may be applied to the ampule 152 in order to cause the ampule to break.

Figure 7A:
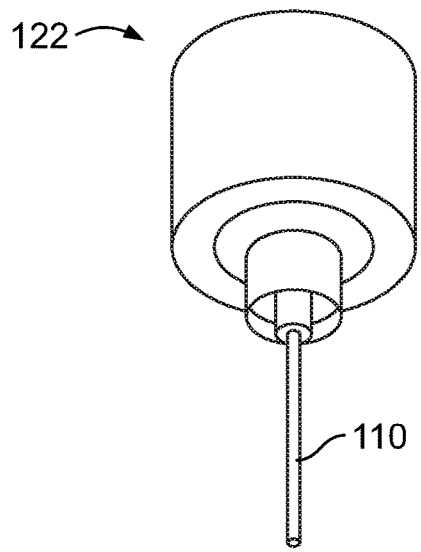
FIGS. 7a-b illustrate, respectively, a perspective view and a top view of an example second compartment of the example autoinjector of FIG. 1, according to an example embodiment.
Figure 7B:
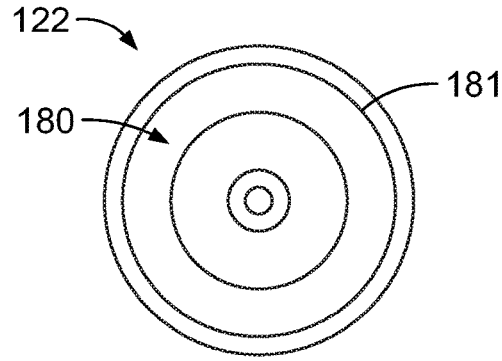

After the ampule 152 breaks, medicament from the ampule 152 flows from the ampule 152 to the second compartment 122. The second compartment 122 includes a chamber configured to collect the medicament. For instance, as shown in FIG. 7B, second compartment 122 includes an inner chamber 180 into which the medicament flows.

In an example embodiment, the autoinjector 100 includes at least one channel between the first compartment 112 and the second compartment 122 through which the medicament flows. For instance, with reference to FIG. 6, spike assembly 168 includes a plurality of holes 169 on a proximal end of the spike assembly 168 and a plurality of channels 170a-b on a distal end of spike assembly 168. After the ampule 152 is broken, medicament will flow from the first compartment 112, through holes 169 to channels 170a-b and then to second compartment 122.

In an example embodiment, the autoinjector 100 includes one or more one-way valves positioned between the first compartment 112 and second compartment 122. For instance, in an example embodiment, with reference to FIG. 6B, channels 170a-b include one-way valves 182a-b. Such one-way valves may help to prevent medicament from flowing from the second compartment 122 back to the first compartment 112.

However, in other examples, such one-way valves are not included in the autoinjector. In an example embodiment, the first compartment 112 and the second compartment 122 are configured to be airtight or substantially airtight, and this may reduce or eliminate a need for one-way valves between the compartments. For instance, in an example embodiment, activation of the first trigger 108 causes the first compartment 112 and the second compartment 122 to become substantially airtight. With reference to FIG. 5, the cap 121 comprises a seal 190 (e.g., an O-ring) around an outer surface 192 of the cap 121. Further, the cap 121 is configured to, upon the application of force to the cap, move in the distal direction 128 relative to the main body 114 of the first compartment 112 and cause the seal 190 to interact with an inner surface of the main body of the first compartment to make the first compartment and the second compartment substantially airtight. In particular, the seal 190 will interact with an inner sidewall 167 (see FIG. 4) of the first compartment 112 to make the first compartment 112 airtight. In an example embodiment, making the compartments substantially airtight helps to force the medicament flow from the first compartment 112 to the second compartment 122 when the ampule 152 is broken.

By the term "substantially" it is meant that the recited characteristic need not be achieved exactly, but that deviations or variations, including for example, tolerances, measurement error, measurement accuracy limitations and other factors known to skill in the art, may occur in amounts that do not preclude the effect the characteristic was intended to provide. In an example embodiment, "substantially airtight" means that less than 0.5% of the air within the first compartment 112 and the second compartment 122 is able to escape the first compartment 112 and the second compartment 122.

In an example embodiment, the autoinjector 100 includes a filter configured to block solid particulates of a threshold size from entering at least one of the second compartment 122 and the output needle 110. In an example embodiment, the threshold size is approximately 100 microns, and thus the filter blocks solid particulates of approximately 100 microns or more from entering at least one of the second compartment 122 and the output needle 110. In another example, the threshold size is approximately 50 microns. In yet another example, the threshold size is approximately 10 microns. Other example threshold sizes are possible as well. Such a filter helps to prevent shards of glass from the broken ampule 152 from entering the second compartment 122 and the output needle 110. In an example embodiment, channels 170a-b include the filter. In another example, holes 169 in the spike assembly 168 each include a filter. In yet another example, the second compartment 122 includes a filter at the distal end of the second compartment 122. Other example locations of the filter are possible as well.

After medicament flows from the first compartment 112 to the second compartment 122, the medicament may then be automatically injected. Release of the second biasing member 124 serves to automatically inject the medicament. Automatically injecting the medicament is described in further detail with reference to FIGS. 2-4, 6-8, and 10.

As mentioned above, the second biasing member 124 is configured to, upon application of force to the second trigger 126, automatically move the first compartment 112 in the distal direction 128 relative to the outer housing 102 and the second compartment 122 to force medicament from the second compartment 122 to the output needle 110. With reference to FIGS. 2-4, second biasing member 124 is initially compressed around the main body 114 of the first compartment 112. First compartment 112 includes arms 210a-d and the arms include protrusions 212a-d. First compartment 112 also includes a flange 214. Second biasing member 124 is held in a compressed state between protrusions 212a-d and flange 214.

The second trigger 126 may be activated by a user applying force to the needle shield 106. For instance, a user may press the needle shield 106 against an injection site in order to apply a force to move the needle shield 106 in proximal direction 129. Needle shield 106 includes arms 216a-d (see FIG. 8). These arms 216a-d interact with flange 218 (see FIGS. 2 and 4) on main body 114 of first compartment 112. Movement of the needle shield 106 in proximal direction 129 thus forces the first compartment 112 to also move in the proximal direction 129. Further, as needle shield 106 is moved in the proximal direction 129, the arms 210a-d at the proximal end of the first compartment 112 interact with an inner surface at the proximal end of the outer body 102. This interaction causes the arms 210a-d to deflect radially inward, and this deflection releases the second biasing member 124 from the protrusions 212a-d.

At the same time, arms 216a-d may deflect radially outward, and this allows needle shield 106 to continue to move in proximal direction 129. As a result, output needle 110 then penetrates the injection site up to a given depth. In an example embodiment, the autoinjector 100 includes one or more stop features that limit the movement of the needle shield 106 relative to outer body 102. For instance, in an example embodiment, needle shield 106 includes cutouts 220 (see FIG. 8) that limit the distance needle shield 106 is able to slide relative to the outer body 102 when the autoinjector 100 is pressed against the injection site. Cutouts 220 may thus help to control the needle penetration depth.

Figure 10:
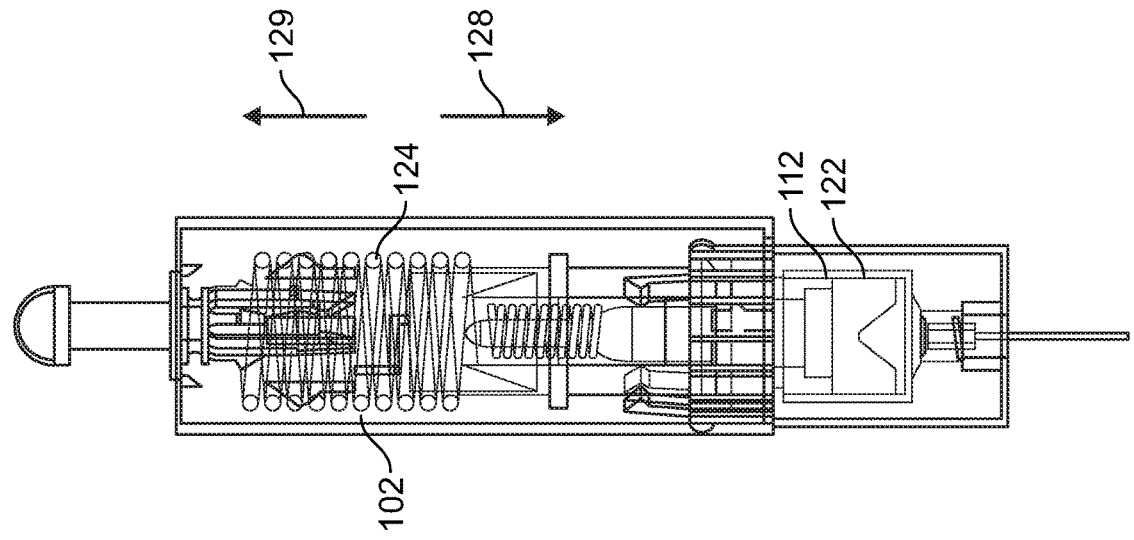
FIG. 10 illustrates a side view of various components of the example autoinjector of FIG. 1 during an injection process, according to an example embodiment.
Figure 8:
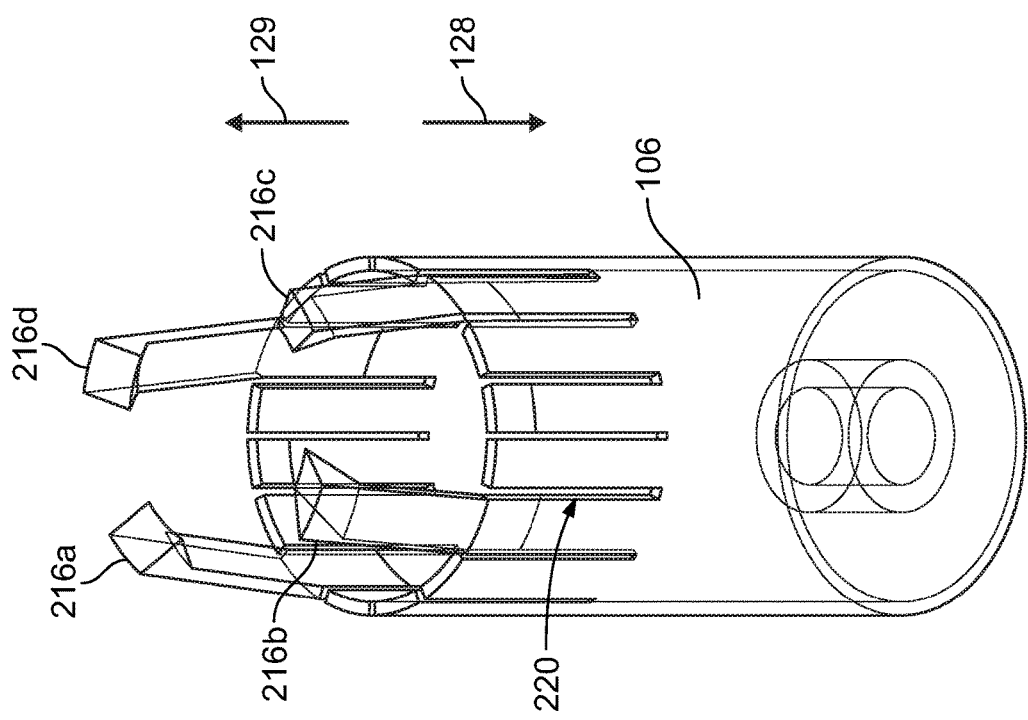
FIG. 8 illustrates a perspective view of an example needle shield of the example autoinjector of FIG. 1, according to an example embodiment.

When the second biasing member 124 is released, the second biasing member 124 moves the first compartment 112 in distal direction 128 relative to the outer body 102 and the second compartment 122 (see FIG. 10). The first compartment 112 thus acts as a mechanical piston moving through the second compartment 122, so as to force medicament from the second compartment 122 to the output needle 110. In particular, the distal end of the spike assembly 168 acts as a piston. In an example, since the first compartment 112 and second compartment 122 are substantially airtight, the movement of the spike assembly 168 through the second compartment 122 decreases the volume of the chamber 180 in the second compartment 122, which results in increased air pressure and forces medicament from the second compartment 122 to the output needle 110.

In the example shown in FIG. 10, spike assembly 168 is slidably engaged with the sidewall 181 (see FIG. 7b) of the chamber 180 of the second compartment 122. Therefore, as spike assembly 168 moves along sidewall 181, the volume of chamber 180 is reduced and medicament is forced from the second compartment 122 to the output needle 110. However, other examples of forcing medicament out of the second compartment 122 are possible as well. For instance, in another example embodiment, the second compartment 122 includes a flexible reservoir, and the movement of the first compartment 112 relative to the second compartment 122 forces the flexible reservoir to collapse, thereby forcing medicament from the second compartment 122 to the output needle 110.

In other example embodiments, rather than the first compartment 112 moving relative to the outer body 102 and the second compartment 122 to force the medicament from the second compartment 122, autoinjector 100 may force the medicament out of the second compartment 122 in other ways. For instance, in an example embodiment, the second biasing member 124 is configured to compress a flexible reservoir of the second compartment 122 radially inward, thereby forcing medicament from the second compartment 122 to the output needle 110. Other examples of forcing medicament from the second compartment to the output needle 110 are possible as well.

As shown in FIGS. 2-3, biasing member 124 is a spring. Any suitable spring may be used. In an example embodiment, the spring constant is approximately 3-8 lbs/in and the spring provides approximately 3-8 lbf. Other example spring constants and pounds of force are possible as well.

In an example embodiment, the autoinjector 100 is configured to allow injection of a fixed volume or dose, so as to provide dose accuracy and reduce or minimize the risk of underdosing and/or overdosing. As a general matter, the autoinjector may be configured so as to prevent liquid from flowing from the second compartment 122 to the output needle 110 after a fixed amount has been delivered through the output needle 110. Preventing liquid from flowing from the second compartment 122 to the output needle 110 after a fixed amount has been delivered through the output needle 110 may be achieved in various ways. For instance, in an example embodiment, the size of the second compartment second compartment limits the size of the fixed dose to be delivered. In another example embodiment, the second compartment 122 may be larger than the size of the fixed dose to be delivered, but the movement of the first compartment 112 relative to the second compartment is limited to a fixed amount. In order to limit the movement of the first compartment 112 relative to the second compartment, the autoinjector 100 may include one or more stop features (e.g., protrusions) that limit movement of the first compartment 112 in the distal direction 128. By limiting the movement of the first compartment 112 relative to the second compartment to a fixed amount, the autoinjector will only force a fixed amount of the medicament from the second compartment 122 to the output needle 110.

The autoinjector 100 may be used for various purposes such as therapeutic, diagnostic, preventative, or vaccination purposes. Further, the autoinjector 100 may be configured for various different types of injections. For instance, in an example embodiment, autoinjector 100 is configured for intramuscular, intravenous, subdermal, subcutaneous and/or intraepidermal injections. The needle penetration depth of the autoinjector 100 may be selected based on the desired type injection. In an example embodiment, the needle penetration depth of the autoinjector 100 is determined based on how far the needle shield 106 retracts into outer body 102 when a user forces the needle shield 106 against the injection site. As discussed above, the autoinjector 100 may include one or more stop features that limit the movement of the needle shield 106 relative to outer body 102.

In an example embodiment, the first trigger 108 and the second trigger 126 may be activated by a user at the same or substantially the same time. Further, the autoinjector 100 may be configured so that, when the first and second trigger are activated at the same or substantially the same time, the second compartment fills up with the intended dose of medicament before the medicament is forced from the second compartment 122 to the output needle 110.

In an example embodiment, the properties of the first biasing member 116 and the second biasing member 124 are selected such that the first biasing member 116 forces the ampule 152 to break before the second biasing member 124 forces the first compartment to move relative to the second compartment. In an example embodiment, even when force is applied to the first and second triggers at the same time, the first biasing member is released a threshold amount of time before the second biasing member. For instance, the cap 121 includes a flange 230 (see FIG. 5) and flange 230 may serve as a safety lock so that second biasing member 124 cannot be released until the first trigger 108 is activated. In particular, in an example embodiment, flange 230 prevents arms 210a-d from being deflected radially inward (and thus releasing the second biasing member 124 from its compressed state) until the cap 121 is moved a threshold amount during activation of the first trigger 108. The size and position of flange 230 may also be selected so that the first biasing member 116 is released a threshold amount of time before the second biasing member 124 is released. By being released a threshold amount of time before the second biasing member, the second compartment 122 is able to fill up with the dose of medicament before the first compartment 112 begins moving through the second compartment 122 to force the medicament from the second compartment 122 to the output needle 110.

By the term "substantially" it is meant that the recited characteristic need not be achieved exactly, but that deviations or variations, including for example, tolerances, measurement error, measurement accuracy limitations and other factors known to skill in the art, may occur in amounts that do not preclude the effect the characteristic was intended to provide. In an example embodiment, the first and second triggers are activated at substantially the same time when force is applied by a user to the first trigger and the second trigger within one second of one another. However, in other examples, the time between activation is less. For instance, in another example, the first and second triggers are activated at substantially the same time when force is applied by a user to the first trigger and the second trigger within 0.5 seconds of one another. In yet another example, the first and second triggers are activated at substantially the same time when force is applied by a user to the first trigger and the second trigger within 0.25 seconds of one another. Other examples are possible as well.

Although the first trigger and the second trigger may be activated at the same or substantially the same time, in another example embodiment, the first trigger may be activated well in advance of the second trigger. For instance, the first trigger may be activated minutes, hours, days, or weeks before the second trigger. In such an example, the first compartment 112 and the second compartment 122 may be airtight or substantially airtight, so as to provide a sterile environment for the medicament after the ampule 152 is broken.

Although autoinjector 100 is described as including two separate triggers for the first and second biasing members, in other example embodiments, the autoinjector may have a single trigger. The single trigger may be coupled to both the first and second biasing members, so that activation of the single trigger releases both the first and second biasing members. For instance, in an example embodiment, the autoinjector includes an outer body, a trigger, an output needle, and a first compartment. The first compartment is positioned within the outer body and comprises (i) a main body and (ii) a first biasing member coupled to the trigger. The autoinjector also includes a second compartment positioned in the outer body and in fluid communication with the first compartment and the output needle. Further, the autoinjector includes a second biasing member coupled to the trigger. The first biasing member is configured to, upon application of force to the trigger, automatically move an ampule when loaded in the main body relative to the main body to force the ampule against a portion of the first compartment, so as to break the ampule and allow a medicament within the ampule to flow from the ampule to the second compartment. The second biasing member is configured to, upon the application of force to the trigger, automatically force medicament from the second compartment to the output needle. In an example embodiment, automatically forcing medicament from the second compartment to the output needle comprises automatically moving the first compartment in the distal direction relative to the outer housing and the second compartment to force medicament from the second compartment to the output needle.

FIG. 11 illustrates an example autoinjector 300 having a single trigger. Autoinjector 300 is similar in many respects to autoinjector 100, and thus is not described in as great of detail. It should be explicitly noted, however, that any possibilities and permutations described above with respect to autoinjector 100 may equally apply to autoinjector 300, and vice versa. In particular, autoinjector 300 includes many of the same elements as autoinjector 100; however, rather than including a first trigger 108 and a second trigger 126, autoinjector 300 includes a single trigger 302. In this example, needle shield 106a acts as the single trigger 302. Movement of the needle shield 106a in proximal direction 129 forces first compartment 112 into the cap 121a, so that the arms 160a-d of the cap 121a deflect to release the first biasing member 116. Further, this movement of needle shield 106a also forces the arms 210a-d of first compartment 112 to deflect to release the second biasing member 124.

As another example, FIG. 12 illustrates an autoinjector 350 having a single trigger. Autoinjector 350 is similar in many respects to autoinjector 100, and thus is not described in as great of detail. It should be explicitly noted, however, that any possibilities and permutations described above with respect to autoinjector 100 may equally apply to autoinjector 350, and vice versa. In this example of FIG. 12, cap 121b acts as the single trigger. Movement of cap 121b in distal direction 128 forces first compartment 112 into the cap 121b, so that the arms 160a-d of the cap 121b deflect to release the first biasing member 116. Further, this movement of cap 121b also forces the arms 210a-d of first compartment 112 to deflect to release the second biasing member 124.

Although in the examples discussed above, cap 121 and needle shield 106 act as the single trigger and/or the first and second triggers, other triggers for automatically breaking the ampule 152 and automatically injecting the medicament are possible as well. For instance, in other example embodiments, the trigger or triggers comprise a switch, a level, a removable cover, a twistable cap, or a button. Other triggers are possible as well. In another example embodiment, an application of heat is used to break the ampule.

Further, although in the examples discussed above, the first biasing member 116 and the second biasing member 124 are springs, other biasing members are possible as well. For instance, in other example embodiments, the biasing members include a pneumatic-based biasing member (e.g., compressed gas), a magnetic-based biasing member, a motorized biasing member, or a thermochemical-based biasing member. Examples of a magnetic-based biasing member include the use of an electrical current (e.g., a sudden electrical current) to induce an electromagnetic moment to force a magnetic or charged member to impact or crush the ampule, or a mechanical member to disengage and allow one magnetic member to be attracted or repelled against another member to impact and/or crush the ampule. As another example, a motorized biasing member is similar in the use of an electric motor and gear mechanism to induce a force to crush and/or impact the ampule. Other biasing members are possible as well.

Still further, although in the examples discussed above, the first compartment 112 and the second compartment 122 are formed separate from one another, in other examples the first compartment 112 and the second compartment 122 are integral with one another. For instance, in an example, the autoinjector includes a main compartment body that includes a first compartment at a proximal end of the main compartment body and a second compartment at a distal end of the main compartment body.

In an example embodiment, the disclosed autoinjector is compatible with a wide assortment of different ampules, such as ampules suitable for in containing drugs of various masses, volumes, and dynamic viscosities including ranges, for example, from 0.01 mg to 1 g, and/or from 0.01 mL to 1 L, and/or from 0.01 cP to 100 P. Other examples are possible as well. Different injection speeds may be desired for different medicaments and/or medicaments having different viscosities. In an example embodiment, the autoinjector is configured such that the autoinjector achieves a desired injection speed. For instance, in an example embodiment, the properties (e.g., spring size, spring constant, etc.) of the second biasing member 124 may be selected based on the desired injection speed for a particular medicament intended to be used with the autoinjector.

Example methods of automatically injecting medicament from an ampule are also provided. Such methods could, for example, be carried out with the autoinjector 100, autoinjector 300, or autoinjector 350 described with reference to FIGS. 1-12.

Figure 13:
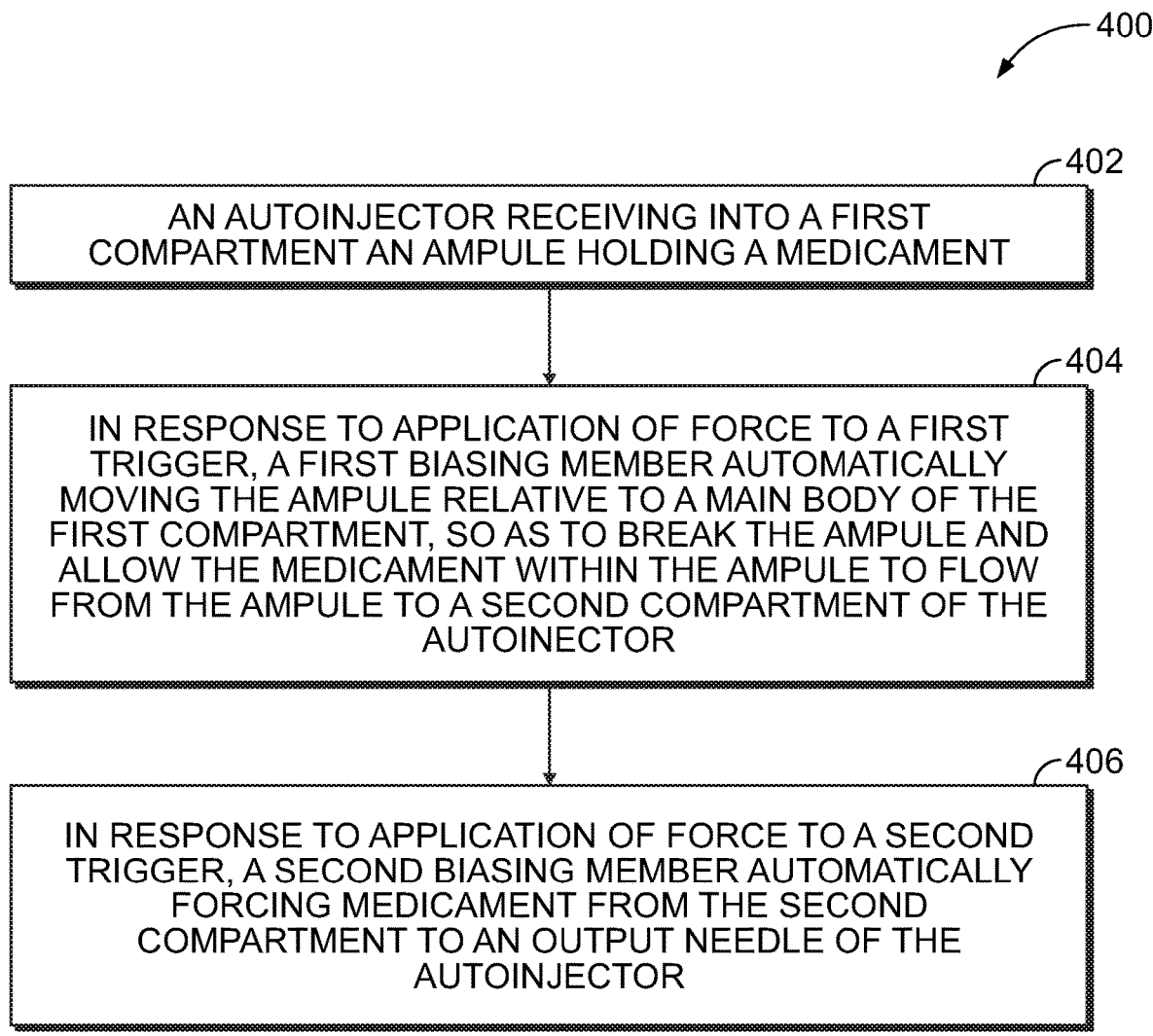
FIG. 13 shows a flowchart of an example method for automatically injecting medicament from an ampule, according to an example embodiment.

FIG. 13 shows a flowchart of an example method 400 for automatically injecting medicament from an ampule. Method 400 shown in FIG. 13 presents an embodiment of a method that, for example, could be carried out with the autoinjector 100 described with reference to FIGS. 1-10. It should be understood that for this and other processes and methods disclosed herein, flowcharts show functionality and operation of one possible implementation of present embodiments. Alternative implementations are included within the scope of the example embodiments of the present disclosure in which functions may be executed out of order from that shown or discussed, including substantially concurrent or in reverse order, depending on the functionality involved, as would be understood by those reasonably skilled in the art.

At block 402, method 400 involves an autoinjector receiving into a first compartment an ampule holding a medicament. At block 404, the method includes in response to application of force to a first trigger, a first biasing member automatically moving the ampule relative to a main body of the first compartment, so as to break the ampule and allow the medicament within the ampule to flow from the ampule to a second compartment of the autoinjector. At block 406, the method further includes in response to application of force to a second trigger, a second biasing member automatically forcing medicament from the second compartment to an output needle of the autoinjector.

In another example, the method of automatically injecting a medicament could be carried out by users of the example autoinjectors described with reference to FIGS. 1-12. In an example, the method includes inserting an ampule holding a medicament into a first compartment of an autoinjector. The method further includes applying force to a first trigger of the autoinjector to release a first biasing member and automatically break the ampule, wherein the first biasing member automatically moves the ampule relative to a main body of the first compartment, so as to break the ampule and allow the medicament to flow from the ampule to a second compartment of the autoinjector. Further, the method includes applying force to a second trigger of the autoinjector to release a second biasing member and automatically inject the medicament, wherein the second biasing member automatically forces medicament from the second compartment to an output needle of the autoinjector.

Example autoinjectors and methods described herein provide improved systems and methods for automatically injecting a medicament (e.g., epinephrine). For instance, the disclosed systems and methods provide a more cost-effective device for automatically injecting epinephrine than current devices on the market for automatically injecting epinephrine. In an example, current autoinjectors in the market for automatically injecting epinephrine range from approximately $70-$500 and must be replaced every 18 months when the epinephrine held within the autoinjector expires. In contrast to the current autoinjectors in the market, the disclosed autoinjector beneficially utilizes medicament ampules such as epinephrine ampules. Epinephrine ampules typically cost on the order of less than a dollar to a few dollars, so utilizing such ampules helps to reduce the cost of automatically injecting epinephrine compared to existing autoinjectors. Further, the disclosed autoinjector also allows a user to remove an ampule if the medicament within the ampule has expired and to reinsert a new ampule in the autoinjector. Thus, it is not necessary for a user to dispose of the entire device in the event that the medicament within the ampule has expired. This ability to replace the glass ampule without disposing of the entire device in the event the epinephrine expires also helps to reduce the cost of automatically injecting epinephrine compared to existing autoinjectors.

Still further, since current devices on the market for automatically injecting epinephrine use drug bottles with a membrane top or a pre-filled syringe, the current devices require aseptic manufacturing. However, the manufacturing of the autoinjector 100 may be less complex by not requiring aseptic manufacturing, which also helps to reduce the cost of automatically injecting epinephrine compared to existing autoinjectors. Yet still further, current autoinjectors for injecting epinephrine are typically classified as drug/device combination and are thus subject to expensive and time consuming regulatory approval processes. The disclosed autoinjector enables an end-user to complete the final assembly by installing the ampule. As a result, the proposed autoinjector may avoid the expensive and time consuming regulatory approval processes to which current autoinjectors are subject.

Another example benefit of the disclosed systems and methods is that the autoinjector provides a user-friendly device that fully automates both the breaking of the ampule and the injection of the medicament. This results in a device providing a simple operation that easily allows the user to operate the autoinjector and inject a medicament such as epinephrine. As mentioned above, in an example the disclosed autoinjector includes a single trigger for automatically breaking the ampule and automatically injecting the medicament. This single trigger provides a simple operation for the user. Further, in another example where the autoinjector includes a first trigger for automatically breaking the ampule and a second trigger for automatically injecting the medicament, the first and second triggers beneficially may be activated either at different times or at the same or substantially the same time. The ability to activate both triggers at substantially the same or to activate a single trigger may be particularly advantageous in an emergency situation such as anaphylaxis. By allowing both triggers to be activated at the same time or substantially the same time, the user may easily operate the device to receive the injection without needing to wait a certain amount of time after activating the first trigger in order to activate the second trigger. This may be particularly advantageous in an emergency situation where the user may be in a high stress situation and an accurate dose should be administered as quickly as possible.

The description of the different advantageous arrangements has been presented for purposes of illustration and description, and is not intended to be exhaustive or limited to the embodiments in the form disclosed. Many modifications and variations will be apparent to those of ordinary skill in the art. Further, different advantageous embodiments may describe different advantages as compared to other advantageous embodiments. The embodiment or embodiments selected are chosen and described in order to explain the principles of the embodiments, the practical application, and to enable others of ordinary skill in the art to understand the disclosure for various embodiments with various modifications as are suited to the particular use contemplated.

What is claimed is:

1. An autoinjector comprising:
an outer body;

a first trigger;
an output needle;
a first compartment, wherein the first compartment is positioned within the outer body, wherein upon application of force to the first trigger, force is applied within the first compartment to allow a medicament to flow to the output needle; and a second compartment is arranged in series with the first compartment such that the second compartment and the first compartment have a common central axis and are longitudinally spaced apart in a first position and the second compartment is positioned in the outer body and in fluid communication with the first compartment and the output needle, wherein the first compartment is configured to move in a distal direction relative to the second compartment.

2. The autoinjector of claim 1, wherein the first compartment comprises: (i) a main body; (ii) a first biasing member coupled to the first trigger; and (iii) a protrusion positioned at a distal end of the main body; and a second biasing member coupled to a second trigger; wherein the second biasing member is configured to, upon application of force to the second trigger, automatically move the first compartment in the distal direction relative to the outer housing and the second compartment to force medicament from the second compartment to the output needle.

3. The autoinjector of claim 2, wherein the autoinjector comprises a cap; wherein a proximal end of the cap is the first trigger; wherein the cap further comprises at least one arm having a protrusion configured to hold the first biasing member in a compressed state; and
wherein the at least one arm is configured to, upon application of force to the cap, deflect to release the first biasing member from the at least one arm having the protrusion.

4. The autoinjector of claim 3, wherein the first compartment comprises an opening.

5. The autoinjector of claim 3, wherein the protrusion comprises a spike.

6. The autoinjector of claim 3, further comprising at least one channel between the first compartment and the second compartment.

7. The autoinjector of claim 3, further comprising a one-way valve positioned between the first compartment and the second compartment.

8. The autoinjector of claim 3, further comprising a filter configured to block solid particulates of a threshold size from entering at least one of the second compartment and the output needle.

9. The autoinjector of claim 3, wherein the first and second biasing members comprise biasing members selected from the group consisting of a spring and a pneumatic-based biasing member.

10. The autoinjector of claim 3, wherein the outer body comprises: a main outer body; and a needle shield slidably engaged with the main outer body.

11. The autoinjector of claim 3, wherein the first trigger is configured such that activation of the first trigger unlocks the second trigger, so as to allow the second trigger to be activated.

12. The autoinjector of claim 3, wherein the cap comprises a seal around an outer surface of the cap; and wherein the cap is configured to, upon the application of force to the cap, move in the distal direction relative to the main body of the first compartment and cause the seal to interact with an inner surface of the main body of the first compartment to make the first compartment and the second compartment substantially airtight.

13. The autoinjector of claim 12, wherein the seal comprises an O-ring.

14. An autoinjector comprising: an outer body; a first trigger; an output needle; a first compartment, wherein the first compartment is positioned within the outer body and comprises (i) a main body and (ii) a first biasing member coupled to the first trigger; a second compartment is arranged in series with the first compartment such that the second compartment and the first compartment have a common central axis and are longitudinally spaced apart in a first position and the second compartment is positioned in the outer body and in fluid communication with the first compartment and the output needle; and a second biasing member coupled to a second trigger;
wherein the second biasing member is configured to, upon application of force to the second trigger, automatically force medicament from the second compartment to the output needle.

15. The autoinjector of claim 14, wherein the autoinjector comprises a cap; wherein a proximal end of the cap is the first trigger; wherein the cap comprises a seal around an outer surface of the cap; and wherein the cap is configured to, upon the application of force to the cap, move in the distal direction relative to the main body of the first compartment and cause the seal to interact with an inner surface of the main body of the first compartment to make the first compartment and the second compartment substantially airtight.

16. The autoinjector of claim 14, wherein the first and second biasing members comprise biasing members selected from the group consisting of a spring and a pneumatic-based biasing member.

17. The autoinjector of claim 14, wherein the second biasing member is configured to automatically move the first compartment in the distal direction relative to the outer housing and the second compartment to force medicament from the second compartment to the output needle.

18. A method of automatically injecting a medicament, the method comprising:
providing an autoinjector;
placing a medicament into a first compartment of the autoinjector;
applying force to a first trigger of the autoinjector, thereby causing the medicament to flow from the first compartment to a second compartment, wherein the second compartment is arranged in series with the first compartment such that the second compartment and the first compartment have a common central axis and are longitudinally spaced apart in a first position; and
automatically moving the first compartment in a distal direction relative to the second compartment, via a second biasing member, and thereby forcing medicament from the second compartment to the output needle.

19. An autoinjector comprising:
an outer body;
a first trigger;
an output needle;
a first compartment, wherein the first compartment is positioned within the outer body, and
a second compartment,
wherein the first compartment is in fluid communication with the second compartment,
wherein the second compartment is arranged in series with the first compartment such that the second compartment and the first compartment have a common central axis and are longitudinally spaced apart in a first position,
wherein the second compartment is positioned in the outer body and in fluid communication the output needle, and
wherein the first compartment is configured to move in a distal direction relative to the second compartment.

* * * * *